(12) United States Patent
Niedermeier

(10) Patent No.: US 8,055,379 B2
(45) Date of Patent: Nov. 8, 2011

(54) DEVICE AND METHOD FOR THE INSPECTION OF CONTAINERS

(75) Inventor: Anton Niedermeier, Offenstetten (DE)

(73) Assignee: Krones AG, Neutraubling (DE)

( * ) Notice: Subject to any disclaimer, the term of this patent is extended or adjusted under 35 U.S.C. 154(b) by 959 days.

(21) Appl. No.: 11/961,523

(22) Filed: Dec. 20, 2007

(65) Prior Publication Data

US 2008/0161947 A1 Jul. 3, 2008

(30) Foreign Application Priority Data

Dec. 27, 2006 (DE) .......................... 10 2006 062 298

(51) Int. Cl.
*G06F 7/00* (2006.01)
(52) U.S. Cl. ........................................................ 700/230
(58) Field of Classification Search .................. 700/230; 198/470.1, 478.1, 471.1, 481.1, 459.2
See application file for complete search history.

(56) References Cited

U.S. PATENT DOCUMENTS

| 3,811,567 | A | * | 5/1974 | Tomita et al. ................... 209/3.1 |
| 4,832,173 | A | * | 5/1989 | Hattori et al. .............. 198/377.1 |
| 5,073,708 | A | * | 12/1991 | Matsumoto et al. ...... 250/223 B |
| 5,607,045 | A | | 3/1997 | Hermann Kronseder et al. |
| 5,743,377 | A | | 4/1998 | Kronseder et al. |
| 7,057,718 | B2 | | 6/2006 | Kwirandt et al. |
| 7,295,317 | B2 | * | 11/2007 | Niedermeier et al. ........ 356/428 |
| 2005/0131563 | A1 | | 6/2005 | Kram et al. |
| 2006/0207859 | A1 | * | 9/2006 | Fiegler ....................... 198/478.1 |

FOREIGN PATENT DOCUMENTS

| DE | 9401926 U | 3/1994 |
| DE | 10133104 | 1/2003 |
| DE | 10164496 | 7/2003 |
| EP | 0726216 | 8/1996 |
| EP | 0743267 A1 | 11/1996 |
| GB | 2001751 | 2/1979 |
| WO | WO-9408230 | 4/1994 |
| WO | WO-2004053471 | 6/2004 |

* cited by examiner

*Primary Examiner* — Ramya Prakasam
(74) *Attorney, Agent, or Firm* — Marshall, Gerstein & Borun LLP

(57) ABSTRACT

An arrangement for inspecting filled and closed containers (F), having a transporting means (3) which transports the containers (F) for a preset distance of travel at a speed of transport $V_{Trans}$ and at which are arranged a plurality of holding elements for the containers (F), the holding elements each being rotatable to set the containers (F) rotating on their longitudinal axes, and having a control means (13) which causes the rotation of the containers on their longitudinal axes to be controlled to follow a preset profile of movement (P) which depends on the position of the containers on the distance of travel, the rotation being accelerated to a preset maximum speed of rotation $V_{Rot\_max}$ in a first preset part (A) of the travel of the containers over the distance of travel and being decelerated in a second preset part (C) of the travel of the containers over the distance of travel. The preset profile of movement (P) can be varied as a function of the speed of transport $V_{Trans}$ of the containers (F).

11 Claims, 3 Drawing Sheets

DEVICE AND METHOD FOR THE INSPECTION OF CONTAINERS

CROSS-REFERENCE TO RELATED APPLICATION

The present application claims the benefit of priority of German Patent Application No. 10 2006 062 298.7 filed Dec. 27, 2006. The entire text of the priority application is incorporated herein by reference in its entirety.

FIELD OF THE DISCLOSURE

The present disclosure relates to a device and a method for inspecting containers and in particular filled and closed containers.

Known from the prior art are a large number of arrangements and methods for inspecting containers. In this way, it is for example known for the bottoms of containers or their closures to be checked. However, there is also a need for containers which have already been filled and closed to be checked, particularly to check whether there are any foreign particles, such for example as chips or splinters or the like, in the filled container.

Known from WO 94/08230 are a method and an arrangement for inspecting transparent containers and their liquid contents. In this case, on a first carousel, the containers are rotated completely about their vertical axis once at a low speed of rotation and when this is done the side-wall is viewed by a camera to allow any damage to be detected. Following this, the speed of rotation is increased to set the liquid rotating and also to swirl any foreign bodies which may be present up off the bottom of the container. Even before they leave the first carousel, the rotary movement of the containers is stopped to allow them then to be handed over, via a first star-wheel, a slowing-down and separating screw and a second star-wheel, to a second carousel on which the containers are inspected, without themselves being rotated on their vertical axes, for foreign bodies in the material with which they are filled by cameras which move with them. However, because of the comparatively long distance between the first carousel and the inspecting means, a problem which crops up in this case is that, particularly when the speeds of travel are low, the liquid which was originally in motion comes to a standstill again, and any foreign bodies which there may be have thus already settled again and cannot therefore be observed reliably.

WO 2004/053471 A1 describes an improvement inasmuch as the containers from the first carousel are transferred directly to a second carousel in which an inspecting unit is arranged. In this way, the distance that has to be traveled before the containers are observed, and hence the time required for this as well, can be reduced. To be more exact, in this arrangement the containers are accelerated in a first rotary carousel in a first part of its turning movement, a certain rotation is maintained in a second part of its travel and in a third part of its travel the rotation of the containers on their own longitudinal axes is decelerated again.

In a more highly developed version of this inspection arrangement, the containers are set rotating by individual electric-motor drives. This arrangement operates with a high reliability of detection when the production output from the inspection arrangement is at a maximum. If however operations take place with a low production output, the problem arises that, by the time the inspecting unit is reached, the rotation of the liquid may already be so low again that there is no longer any swirling up of foreign bodies. At the present time, the speed of rotation of the containers and the liquid in the containers is limited by a large number of factors such for example as the maximum accelerative torque that is possible, the time that the containers spend in the first rotary carousel, and the maximum braking force that can be applied. Regardless of the production output of the inspection arrangement at the time, operations take place in this case with only a single profile of movement, this profile of movement being optimised, as mentioned above, for the maximum production output and always being started, as was also mentioned above, at a point situated close to the point at which the containers are fed into the first carousel and being completed, by initiating the deceleration of the rotation of the containers, at a fixed point spaced away therefrom, i.e. the interval of time from the stopping of the movement of the containers in rotation to the time when the downstream inspection arrangement is reached is lengthened as the production output goes down, because of the deceleration of the rotation, which deceleration is approximately constant over time until a standstill is reached.

SUMMARY OF THE DISCLOSURE

The object underlying the present disclosure is therefore to provide an arrangement and a method for inspecting filled and closed containers which, even at low production outputs and, in general terms, at different production outputs, permits the containers to be inspected for foreign bodies in the liquid in a manner which always remains equally reliable.

The arrangement according to the disclosure for inspecting filled and closed containers has a transporting means which transports the containers for a preset distance of travel at a preset speed of transport and at which are arranged a plurality of holding elements for the containers, at least some of the said holding elements being rotatable (or at least parts of the holding elements being rotatable), to set the containers rotating on their longitudinal axes. Also provided is a control means which causes the rotation of the containers on their longitudinal axes to be controlled to follow a preset profile of movement, the rotation being accelerated to a preset maximum speed of rotation in a first preset part of the travel of the containers over the distance of travel relative to the surroundings and being decelerated, preferably until the rotation comes to a standstill, in an at least second preset part of the travel of the containers over the distance of travel. A part of the travel where the speed of rotation is constant may be situated between the two.

In accordance with the disclosure, the preset profile of movement may be varied as a function of a current speed of transport of the containers.

What is meant by a holding element is elements which arrange the container in a preset position and make it possible for the containers to be rotated. The holding member may also be a rotary plate on which a container is stood. As well as this, the containers may also be, in particular, rotatable gripping elements to hold the containers clamped axially. Such gripping elements may for example take a grip on the head or neck of the containers.

The preset distance of travel for which the containers are transported may be a sector of a circle but it would also be possible for there to be parts of the travel that were in a straight line or were curved in some desired way.

If for example the transporting means takes the form of a carousel, it would be possible for the containers each to be received at a certain angle of rotation by a specific holding element and for example for the rotation of the containers to be initiated at an angular spacing of 30° from the point where the containers are received. Hence, in this embodiment, the rotary movement is started as a function of the position of the container relative to its surroundings, i.e. the profile of rotary movement depends on the position of the containers along the distance of travel.

In the prior art, this profile of movement does not depend on the speed of transport of the containers. Therefore, in the prior art, the rotary movement is always started at the same point, is always accelerated to a preset maximum speed of rotation, is kept rotating at a constant speed of rotation and is then decelerated at a preset deceleration, starting at a fixed point which is always the same. Because it is also always the same constant of deceleration which is used in the prior art, there is also a change, as a function of the speed of transport, in the point at which the container comes to a standstill in respect of its rotation on its own axis. Hence there is a change too, as a function of the speed of transport, in the point at which the liquid inside the container comes to a standstill and, particularly at low speeds of transport, the entire distance of travel to the point where the inspecting means proper are reached is not made use of for the rotary movement of the containers on their own axes.

In comparison with the prior art, the profile of movement is optimized for the maximum production output, i.e. in the time for which the containers remain in the transporting arrangement in, for example, an accelerating carousel, an attempt is made to apply sufficient energy to the product for foreign bodies, such as pieces of glass, within the liquid still to be moving sufficiently by the time the container reaches the downstream inspecting means. Hence, in the prior art, the same energy is applied when production is at a low rate even through the container is in the transporting means for a longer time than at high output. When production is slow, the energy is used up before the container has reached the inspecting unit due the internal losses caused by friction. This problem is particularly relevant in the case of arrangements which are also referred to as full bottle inspection (FBI) arrangements, in which transfers units such as transfer screws are present between the transporting means and the downstream inspecting unit.

By means of the variation, in accordance with the disclosure, of the profile of movement as a function of the speed of transport, it is for example possible for more rotational energy to be introduced into the liquid in the container when the rate of production is low. It would also be possible for the rotation not to be decelerated again until a later point, in order thereby to ensure that any foreign bodies were still being swirled up even at the time of inspection.

So, if the profile of acceleration or profile of movement changes in such a way that appreciably more energy is applied to the respective containers during their dwell time in the transporting means, longer times can also be covered until a downstream inspection carousel is reached. The minimum production output can also be reduced in this way and this simplifies the scheduling of the work to be done by the systems. Due to the longer dwell time in the transporting means, higher speeds of rotation can be achieved while still observing the restrictions which exist such for example as the rotary accelerations which are permissible.

Thus, a 40% increase for example in the speed of rotation, i.e. one from, for example, 600 revolutions per minute to 850 revolutions per minute, has the effect of doubling the level of energy. Theoretically, what has to date been the minimum production output could thus be appreciably reduced, to half its existing level for example, for the same reliability of inspection.

In a preferred embodiment, the control means controls the maximum speed of rotation of the containers on their longitudinal axes as a function of the speed of transport of the containers in the transporting means. In this way, it would be possible for an acceleration process to be performed over a longer period of time and thus for a higher final speed to be obtained for the containers without exceeding the limit on the maximum acceleration which is possible.

In another advantageous embodiment, the position of the second part of the travel relative to the distance of travel can be varied as a function of the speed of transport of the transporting means. In this way, at a low speed of transport for example, the second part of the travel can be shifted further towards the end of the distance of travel, in order to shorten the interval of time until the containers are inspected in this way. To be more exact, at least the point at which the second part of the travel starts, i.e. the point from which the rotation of the containers is decelerated again, can be varied.

In another preferred embodiment, the transporting means is a transporting carousel. What this means is that a plurality of holding elements are so arranged that the containers are transported substantially along a circular line. This being the case, the individual parts of the travel are defined by the respective sectors of a circle which make up this movement. The transporting carousel is also referred to below as an accelerating carousel.

In another advantageous embodiment, the control means causes the first part of the travel to be variable relative to the distance of travel as a function of the speed of transport of the transporting means. By a variation of this kind, the energy introduced into the containers, such for example as for a free rotation of the containers which, looking in the direction of transport, is later, can also be varied.

The present disclosure is also directed to a system for inspecting filled and closed containers which has an arrangement of the kind described above and a second transporting carousel which is provided downstream of this arrangement and at which at least one inspecting means for detecting foreign bodies in the containers is provided. The said inspecting means is the inspecting means described above which checks the contents of the containers for any foreign bodies. The inspections mean is preferably one which operates by a dark-field method. With the help of reflected light, this method enables fine details of structure, and in particular details which scatter light such as splinters of glass or similar foreign matter, to be made visible.

In another preferred embodiment, the second transporting carousel has a plurality of further holding elements to receive the containers, the holding elements of the second transporting carousel taking over the containers directly from the holding elements of the arrangement described above. Handover of the containers from the transporting means to the second transporting carousel which is as time-saving as possible is possible in this way and the loss of time before the inspection of the containers can thus be kept as small as possible. However, there may also be other transporting units provided between the transporting means and the second transporting carousel, such for example as a transfer starwheel.

In another preferred embodiment, the holding elements of the second transporting carousel take hold of the containers by a circumferential wall of the containers. In this way, it is possible for the bottom of the container to be observed without the observation being interfered with by the holding elements of the second transporting carousel.

The present disclosure is also directed to a method of inspecting closed and filled containers. In a first step of the method, the containers are handed over to a first transporting means in this case. In a further step of the method, the containers are transported by the first transporting means over a preset distance of travel at a preset speed of transport. Also, during the transportation of the containers, they are rotated on their longitudinal axes, with the profile of movement for the rotation depending in a preset way on the position of the containers along the distance of travel relative to the surroundings. In a first preset part of the travel, the rotation of the containers is accelerated to a preset maximum speed of rotation along the distance of travel relative to the surroundings, and in a further preset part of the travel of the containers along the distance of travel it is decelerated and preferably decelerated to a standstill. However, as well as a rotation of the containers on their longitudinal axes, what is also possible is a rotation of the containers on axes which differ slightly therefrom, i.e. on axes which are offset sideways therefrom or axes which are obliquely arranged. In addition, what would also be conceivable in principle would be another kind of movement to produce motion of the liquid relative to the container, such for example as a shaking movement or the like.

In accordance with the disclosure, the preset profile of movement is controlled as a function of the speed of transport of the first transporting means. Advantageously, the maximum speed of rotation is controlled as a function of the speed of transport. The control is advantageously performed in this case in an inverse relationship, i.e. at a lower speed of transport the maximum speed of rotation is increased and conversely, at a higher speed of transport the maximum speed is reduced.

In another advantageous variant, the position of the second part of the travel relative to the surroundings is controlled as a function of the speed of transport of the first transporting means.

In another advantageous variant, the speed of rotation of the containers is increased to a maximum speed of rotation at a preset acceleration starting from the first part of the travel and the acceleration is controlled by taking account of the speed of transport of the first transporting means. In this case it is possible in particular for a subsidiary position to be defined at which an acceleration process for the rotation of the containers is completed. It is also possible for a subsidiary position to be defined at which a deceleration of the rotation of the containers is initiated. The location of these subsidiary positions too may be variable in this case as a function of the speed of transport of the first transporting means.

The speed of rotation of the containers is preferably kept substantially constant between the first part of the travel and the second part of the travel. Particularly even acceleration of the liquid in the containers can be achieved in this way.

BRIEF DESCRIPTION OF THE DRAWINGS

Further advantages and embodiments can be seen from the accompanying drawings.

In the drawings.

DETAILED DESCRIPTION

Figure 1:
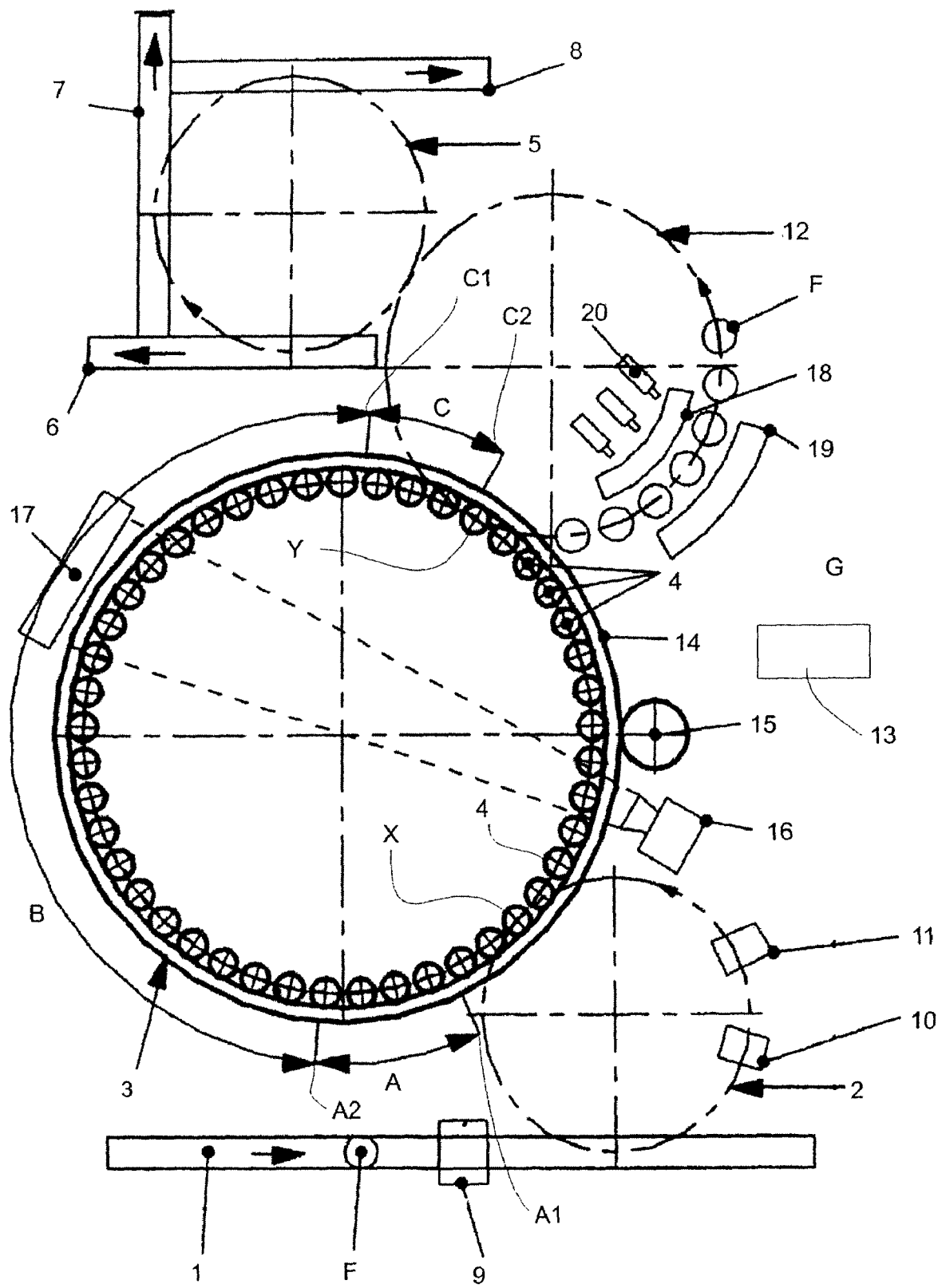
FIG. 1 shows a system according to the disclosure for inspecting containers.

The arrangement for inspecting filled and closed containers (these are beverage bottles in the present case) which is shown schematically in FIG. 1 is set up specifically for inspecting bottles made of transparent or semi-transparent material. On for example a bottle-filling and closing machine situated upstream, the bottles F to be checked are fed, preferably continuously, to an infeed star-wheel 2 by an infeed conveyor belt 1.

When this is done, before they taken over by the infeed star-wheel 2, the bottles travel past an infeed control point 9, which infeed control point 9 is arranged in a fixed position and checks for the presence of a closure and, if required, also checks the height to which the container is filled. To prevent the containers from undergoing excessive accelerations, which might lead in turn to the inspecting units being fouled by liquid slopping over from bottles which have not been closed, any such bottles F which have not been properly closed are not taken hold of by the infeed star wheel 2 and merely pass it by in a tangential direction on their way to a downstream collecting point. The procedure with underfilled and overfilled bottles is the same.

The infeed star-wheel 2 is driven continuously in the anti-clockwise direction in the present case and has a plurality of gripping elements, which are preferably arranged at a uniform spacing representing the pitch of the machine and which are selectively actuatable, for taking hold of the bottles by their bodies and preferably by their head or neck regions too. These gripping elements are selectively actuatable and can be adjusted to different diameters of bottle.

During the transfer from the infeed conveyor belt 1 to a transporting means 3 which follows it in the direction of circulation, the bottles are first moved, with their bottoms clear, across a stationary air-blasting means 10 for bottle bottom for removing soap foam or the like and across a bottom-checking station 11 for detecting fouling on or damage to the bottoms of the bottles, which bottom-checking station 11 is arranged downstream of the means 10 and can be operated by the light-field method. The bottom-checking station 11 is also used for detecting heavy foreign bodies which cannot be swirled up by rotating the bottles.

The actual form that the infeed star-wheel 2 takes is known from the prior art and will therefore not be explained in detail. In this way, the reader is referred to, for example, European patents 0 726 216 B1 and 0 743 267 B1 for the infeed star-wheel 2, to German utility model 94 01 926 U1 for the air-blasting means for bottle bottoms and to German patent application 101 33 104 for the bottom-checking station 11. The disclosure content of WO 2004/053471 which was mentioned earlier is also hereby explicitly incorporated by reference.

At the point X where the pitch circles of the infeed star-wheel 2 and the transporting means 3, which latter rotates in the clockwise direction, meet, the bottles F are transferred by their bottom faces to rotary plates 4 which are mounted to be rotatable in the transporting means 3 on vertical axes, and the bottles F are held in an axial clamping means to be rotatable. This too is known from the prior art.

As the process continues, the bottles which are standing upright on the rotary plates 4 are first set rotating on their longitudinal axes with a continuous acceleration as they pass through the first sector through which they circulate, or the first part of their travel, A, on the transporting means 3 before then travelling through part B of their travel at a defined maximum speed of rotation. This part B of their travel is followed by a sector through which they circulate, or a part of their travel, C, in which the rotation of the bottles is braked, preferably continuously, approximately to a standstill.

In the embodiment shown in FIG. 1 each rotary plate 4 has a pinion (not shown) situated at the bottom which is mounted on a shaft to be rotatable and which meshes with the inner teeth of a toothed ring 14 which has both inner and outer teeth, the said toothed ring being supported on the bed-plate G of the machine by a centreless connection for rotary movement employing ball bearings. The toothed ring 14 can be driven by a driving gear 15 which engages with its outer teeth, under the control of a variable-speed drive. This drive may be an electric motor or the like. The drive takes place in the anti-clockwise direction and thus in the opposite direction to the carousel or transporting means 3.

This movement in opposite directions makes possible sufficiently high rotation on the part of the rotary plates 4. However, in a preferred embodiment it would also be possible for the rotary plates 4 each to be driven separately by separate drive means such as electric motors, in order in this way to obtain individual control of the individual rotations of the bottles. It would also be possible for a plurality of rotary plates 4, such for example as the rotary plates 4 in a given sector of the transporting means 3, to be controlled together at a given time. In the embodiment shown in FIG. 2, it is also possible for controllable magnetic couplings to be provided for each rotary plate 4 which, as the rotary plates travel through the above-mentioned sectors of circulation or parts A, B, C, transmit the torque to be transmitted at an appropriately greater or lesser intensity and in this way make it possible for the rotary movement of the individual rotary plates to be individually controlled. The said magnetic coupling corresponds to the magnetic couplings which are described in WO 2004/053471 and will therefore not be described in detail.

Reference numeral 17 denotes a luminous screen for sidewalls which is arranged on the outside of the transporting means 3. Provided in addition to this is a side-wall camera 16 which is situated diametrically opposite the luminous screen 17 for the side-walls. What is made possible in this way is light-field inspection in transmitted light, by which means darkenings for example caused by damage or fouling can be detected.

The end region of part C of the travel on the transporting means 3 is at a tangent to a second transporting carousel 12 which, in the same way as the infeed star-wheel 2, has at its periphery a plurality of gripping elements, which are arranged to be offset from one another by a distance representing the pitch of the machine and which are selectively controllable, for taking hold of the bottles by their body and/or, if required, by their head or neck region.

In this way, the bottles F can be taken hold of at the common point of contact Y with the first transporting means 3 and can be transferred in the anti-clockwise direction towards a downstream sorting star-wheel 5 with their bottoms clear. On the way there, the bottles F are subjected to detection of foreign bodies by the dark-field method by which foreign bodies which scatter light, and in particular transparent splinters of glass, can be detected.

For this purpose, there are arranged on the two sides of the curved path around which the bottles F circulate equidistant luminous screens 18 and 19 which are matched to the curvature of the path and between which the bottles F travel through freely and, as they do so, can be illuminated laterally over as large an area as possible.

Because of the tunnel-like lighting which takes place simultaneously on both sides, it is possible for a very large amount of light to be introduced into the bottles, which is advantageous particularly with cloudy or dark liquids such for example as yeast-containing beer or cola.

The luminous screens 18 and 19 are preferably fitted with a plurality of LED's which can be operated in a pulsed manner by a lighting control system.

As well as this, the second transporting carousel 12 is also fitted with cameras 20 which are arranged below its gripping elements (not shown), there being for example one camera provided for each gripping element, which cameras circulate with the gripping elements in synchronized positions and observe the bottoms of the bottles as they are illuminated. This arrangement produces dark-field illumination in which light-scattering flaws or foreign bodies show up as light points or zones in an otherwise dark image.

Foreign bodies in the liquid can also be distinguished from foreign bodies or flaws in the container itself by this procedure. While the bottles are moving in the second carousel 12, foreign bodies in or damage to the container itself remain substantially stationary. Foreign bodies in the liquid on the other hand will change position as a function of time, provided the liquid is still moving relative to the bottles.

What would also be conceivable as an alternative would be a stationary arrangement of one or more cameras, in which case triggering which would otherwise be required can advantageously be dispensed with by actuating the cameras 20 for picking up images, and the LED's in the screens 18 and 19, simultaneously.

Reference numeral 5 denotes a sorting star-wheel which likewise has a plurality of selectively controllable gripping elements (not shown). By this sorting star-wheel, the bottles which have been inspected can be dispensed onto different conveyor belts as a function of the results of the checks made by the bottom-checking station 11, the side-wall camera 16 and the cameras 20 which look at the bottles F through their bottoms. In this way, the bottles which are passed as satisfactory can for example leave the inspection machine on the outfeed conveyor belt marked 6, whereas bottles which have faults can be conveyed out on the selective outfeed conveyor belt 7 or 8, as desired, depending on the fault which is detected.

However, as mentioned above, a prerequisite for the effective discovery of the presence of foreign bodies in the liquid is that the liquid also has to be moving relative to the containers, or in other words the foreign bodies still have to be being swirled up when observation by the cameras 20 takes places.

Reference numeral 13 denotes a control means which controls the profiles of movement of the gripping elements, i.e. the rotation of the bottles on their longitudinal axes.

Figure 2:
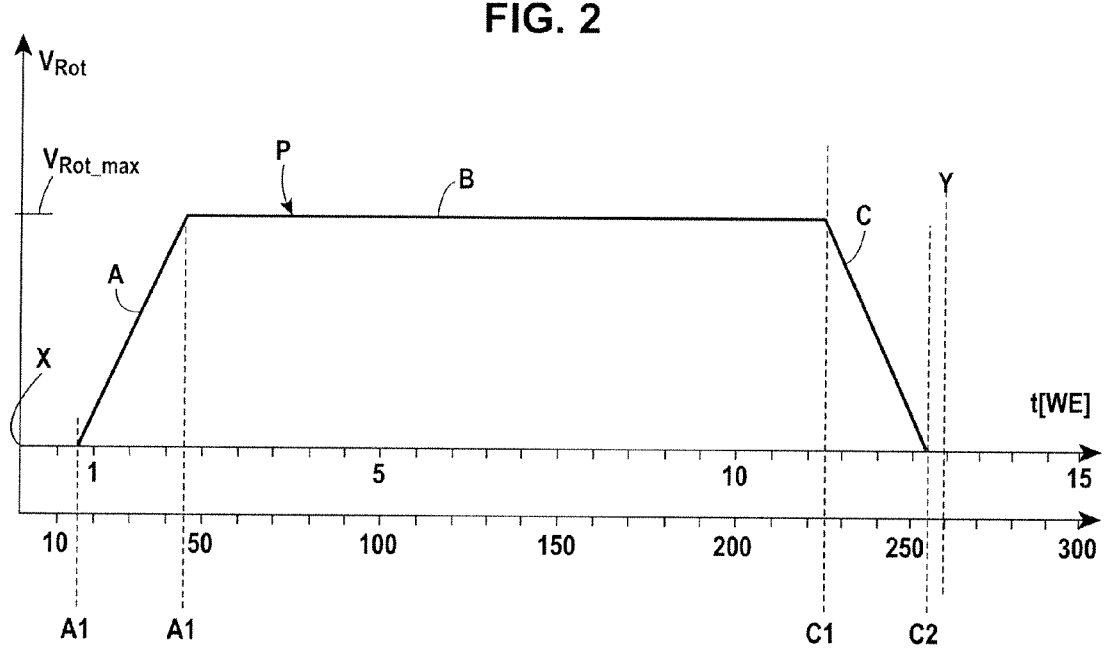
FIG. 2 shows a constant profile of movement from the prior art.

FIG. 2 shows a line defining a prior art profile for a movement whose location is fixed and which is constant (at maximum output).

In this case, the individual parts A, B, C correspond to the parts of the travel A, B, C which are shown in FIG. 1 and a scale in degrees has been shown along the lower X-axis, with the 0° position indicating the position X at which the handover of the bottles from the infeed star-wheel 2 to the transporting means 3 takes place, and the 260° position indicating the position Y at which the handover of the bottles from the transporting means 3 to the second carousel 12 takes place.

In part A of the travel, the bottles are rotated about the line indicating their longitudinal direction and, when this is done, are, as can be seen from FIG. 2, accelerated to a maximum speed $V_{Rot\_max}$. To be more exact, the rotation of the bottles is started at the fixed point identified by line A1 and is speeded up at a constant acceleration until point A2 is reached. Point A1 is thus situated at approximately 15° (see the lower X-axis) regardless of the speed of transport $V_{Trans}$.

In part B, which extends over approximately 180° in the present case, the rotation of the bottles is kept substantially constant, as can likewise be seen from FIG. 2. Finally, in part C of the movement, the rotation of the bottles is decelerated again. The vertical line at C2 indicates, inwards, the position at which the rotation of the bottles has substantially stopped again. Shortly after this position, the bottle is handed over, as mentioned above, to the second transporting carousel 12. In the prior art, the profile of movement P shown in FIG. 2 is constant and not dependent on the speed of transport.

What this means is that the movement depends only on the position of the bottle at any given time. The upper X-axis is a scale for time which is divided into random units of time. When the transporting means 3 moves at this speed of transport $V_{Trans}$, the containers cover a circumferential angle of 100° in five units of time.

Figure 3:
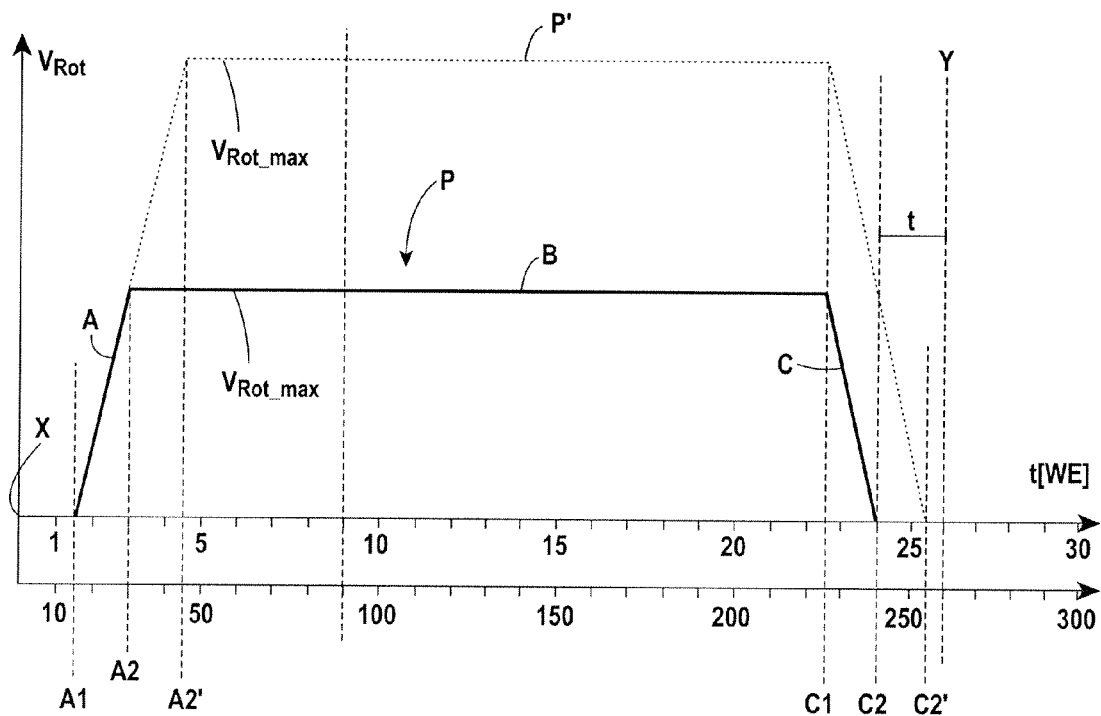
FIG. 3 illustrates the change according to the disclosure in the profile of movement.

FIG. 3 shows operation in a different situation where the speed of transport $V_{Trans}$ of the transporting means 3 is reduced by half. This can be seen in particular from the upper X-axis, on which 30 units of time, or twice the total amount, are required for the complete movement. However, in this case too the acceleration of the containers is started at the same angular position (point A1), and the deceleration of the rotary movement is likewise decelerated at the position identified as C1.

However, because, as mentioned above, the acceleration of the speed of rotation $V_{Rot}$ is always kept constant in the prior art and corresponds for example to the maximum acceleration which is possible, the maximum speed of rotation is reached at an earlier angular position in this case than it would be at the full speed of transport. This is shown in FIG. 3 by the steeper gradient of the profile of movement P in part A of the travel. The acceleration is defined, as is usual, by the change in speed per unit of time. However, in the prior art the profile of movement is thus not dependent on the speed of transport $V_{Trans}$, because the points A1 and C1 at which the acceleration and deceleration respectively of the rotary movement are begun are each fixed. Thus, as can be seen by referring to FIG. 3, what is meant by a profile of movement which is dependent on the position of the bottles is that those points along the part of the travel at which the rotary movement is respectively accelerated and decelerated are fixed in the given case.

It can be seen that there is a certain interval of time Δt between the point at which the containers are at a standstill (position C2) and the position Y. This interval of time is caused by the lower speed of transport $V_{Trans}$ and in the worst case may result in the liquid in the containers having already come to a standstill at the moment at which the containers pass the inspecting means 20, i.e. the cameras. This is particularly true if the speed of transport $V_{Trans}$ of the transporting means 3 is slowed down even further.

Therefore, in accordance with the disclosure, the profile of movement B is varied by taking account of the speed of transport of the transporting means 3. Because the accelerative force and the braking force are limited, it is possible, as indicated by reference numeral P', for the maximum speed of rotation $V_{Rot\_max}$ to be increased. This is shown in FIG. 3 by the example of a doubling of the maximum speed of rotation $V_{Rot\_max}$. What the doubling also achieves in this case is that the containers are just coming to a halt at the moment of handover (position C2'). However, it is also ensured that the liquid in the containers is still moving when the bottles pass the inspecting means 20.

Figure 4:
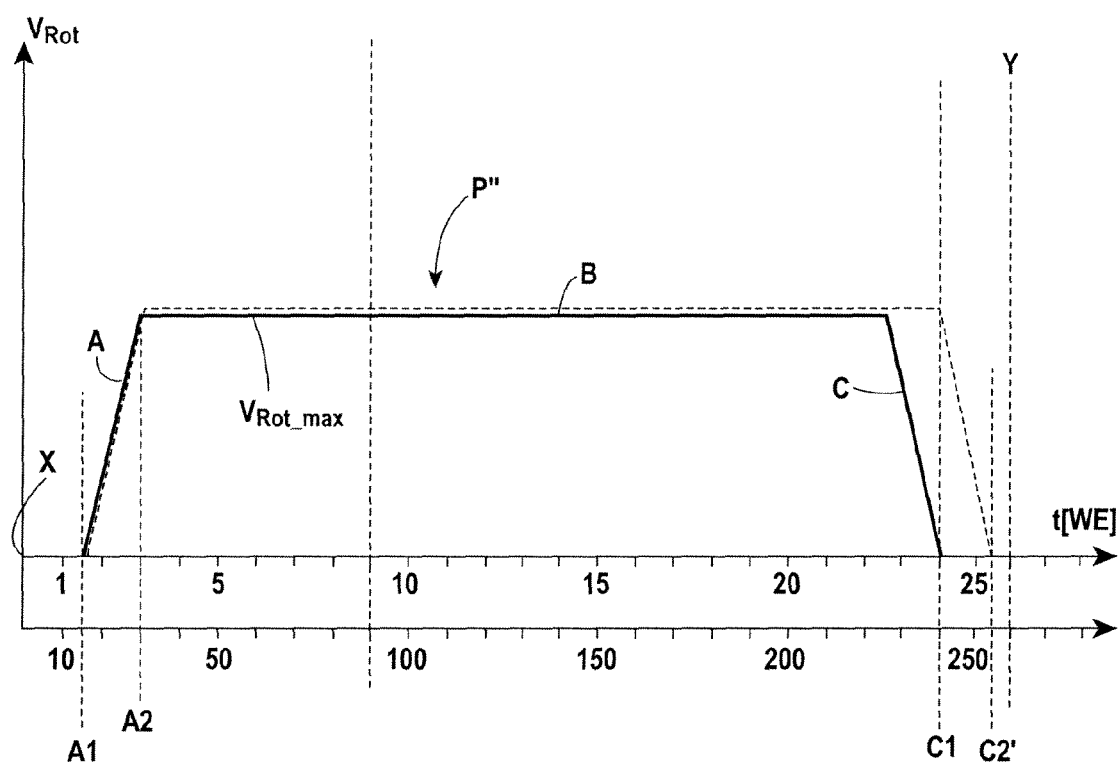
FIG. 4 shows a further change according to the disclosure in the profile of movement.

Shown in FIG. 4 is a further possible way in which a variation in the profile of movement of this kind can be made. In this case the deceleration or braking process has been shifted by a certain displacement in time Δt in order to ensure in this case too that the bottles do not come to a halt until the moment of handover to the second carousel 12, or shortly before this moment (position C2'). The corresponding profile of movement is identified by reference numeral P'''. To make things clear, the profile of movement, part of which lie exactly on top of the profile of movement P, has been offset slightly. However, combinations of the two profiles of movement P' and P''' are also possible if required by the particular application. In this way, on the one hand the maximum speed of rotation $V_{Rot\_max}$ can be increased slightly and on the other hand the time at which the deceleration is initiated can also be shifted slightly.

Thus, in both the method shown in FIG. 3 and the method shown in FIG. 4, the position C2 is moved closer to the Y or, in other words, the rotation of the bottles on their longitudinal axis is stopped at a position C2' which lies closer to the position Y than is the case in the prior art.

All the features claimed in the application documents are claimed as essential to the disclosure provided they are novel and inventive over the prior art either individually or in combination.

The invention claimed is:

1. Arrangement for inspecting filled and closed containers (F), comprising:
    a transporting means (3) which transports the containers (F) for a preset distance of travel at a speed of transport VTrans and at which are arranged a plurality of holding elements for the containers (F), the holding elements each being rotatable to set the containers (F) rotating on their longitudinal axes,
    a control means (13) which causes the rotation of the containers on their longitudinal axes to be controlled to follow a preset profile of movement (P) which depends on the position of the containers on the distance of travel, the rotation being accelerated to a preset maximum speed of rotation VRot-max in a first preset part (A) of the travel of the containers over the distance of travel and being decelerated in a second preset part (C) of the travel of the containers over the distance of travel, and the preset profile of movement (P) is variable as a function of the speed of transport VTrans of the containers (F), wherein the control means (13) controls the maximum speed of rotation VRot-max of the containers on their longitudinal axes as a function of the speed of transport VTrans of the containers in the transporting means (3).

2. Arrangement according to, claim 1, wherein at least the position of the second preset part (C) of the travel relative to the distance of travel can be varied as a function of the speed of transport VTrans of the transporting means.

3. Arrangement according to claim 1, wherein the transporting means (3) is a transporting carousel (3).

4. Arrangement according to claim 1, wherein the control means causes the first preset part (A) of the travel to be variable relative to the distance of travel as a function of the speed of transport VTrans of the transporting means (3).

5. System (10) for inspecting filled and closed containers, having an arrangement according to claim 1 and having a second transporting carousel (12) which is provided downstream of this arrangement and at which at least one inspecting means (18, 19, 20) for detecting foreign bodies in the containers is provided.

6. System according to claim 5, wherein the second transporting carousel (12) has a plurality of further holding elements to receive the containers (F), the holding elements of the transporting carousel taking over the containers directly from the holding elements of the arrangement.

7. System according to claim 6, wherein the holding elements of the transporting carousel (12) take hold of the containers (F) by a circumferential wall of the containers.

8. Method of inspecting closed and filled containers, comprising the following steps:
- handover of the containers to a first transporting means (3);
- transport of the containers by the first transporting means (3) over a distance of travel at a preset speed of transport VTrans; and
- rotation of the containers on their longitudinal axes following a profile of movement (P) which depends on the position of the containers along the distance of travel, the rotation being accelerated to a preset maximum speed of rotation VRot-max in a first preset part (A) of the travel of the containers along the distance of travel relative to the surroundings, and being decelerated in a second preset part (C) of the travel of the containers along the distance of travel, and the preset profile of movement (P) is controlled as a function of the speed of transport VTrans of the first transporting means (3), wherein the maximum speed of rotation VRot-max is controlled as a function of the speed of transport VTrans.

9. Method according to claim 8, wherein the position of the second part (C) of the travel is controlled relative to the surroundings as a function of the speed of transport VTrans of the first transporting means (3).

10. Method according to claim 8, wherein the speed of rotation of the containers is increased to a maximum speed of rotation VRot-max at a preset acceleration starting from the first part (A) of the travel and the acceleration is controlled by taking account of the speed of transport VTrans of the first transporting means (3).

11. Method according to claim 8, wherein the speed of rotation is kept substantially constant between the first part (A) of the travel and the second part (C) of the travel.

* * * * *